United States Patent
Bencsik et al.

(10) Patent No.: US 8,853,216 B2
(45) Date of Patent: *Oct. 7, 2014

(54) HYDROXYLATED PYRIMIDYL CYCLOPENTANE AS AKT PROTEIN KINASE INHIBITOR

(75) Inventors: Josef Bencsik, Boulder, CO (US);
James F. Blake, Boulder, CO (US);
Nicholas C. Kallan, Boulder, CO (US);
Ian S. Mitchell, Boulder, CO (US);
Keith L. Spencer, Boulder, CO (US);
Dengming Xiao, Boulder, CO (US); Rui Xu, Boulder, CO (US); Christine Chabot, South San Francisco, CA (US); Steven Do, South San Francisco, CA (US); Jun Liang, South San Francisco, CA (US); Brian Safina, South San Francisco, CA (US); Birong Zhang, South San Francisco, CA (US); James Graham, Boulder, CO (US)

(73) Assignees: Array BioPharma, Inc., Boulder, CO (US); Genentech, Inc., South San Francisco, CA (US)

( * ) Notice: Subject to any disclaimer, the term of this patent is extended or adjusted under 35 U.S.C. 154(b) by 446 days.

This patent is subject to a terminal disclaimer.

(21) Appl. No.: 12/811,983

(22) PCT Filed: Jan. 9, 2009

(86) PCT No.: PCT/US2009/030602
§ 371 (c)(1),
(2), (4) Date: Jul. 7, 2010

(87) PCT Pub. No.: WO2009/089453
PCT Pub. Date: Jul. 16, 2009

(65) Prior Publication Data
US 2010/0292244 A1    Nov. 18, 2010

Related U.S. Application Data

(60) Provisional application No. 61/020,087, filed on Jan. 9, 2008.

(51) Int. Cl.
| | | |
|---|---|---|
| *C07D 239/70* | (2006.01) | |
| *A61K 31/517* | (2006.01) | |
| *A61P 35/00* | (2006.01) | |
| *A61P 29/00* | (2006.01) | |
| *A61P 25/00* | (2006.01) | |
| *A61P 9/00* | (2006.01) | |
| *A61P 15/02* | (2006.01) | |
| *A61P 17/00* | (2006.01) | |

(52) U.S. Cl.
CPC .................... *C07D 239/70* (2013.01)
USPC ...................... 514/252.16; 544/253

(58) Field of Classification Search
CPC .............. C07D 239/70; A61K 31/519

USPC ...................... 544/253; 514/252.16
See application file for complete search history.

(56) References Cited

U.S. PATENT DOCUMENTS

| 3,885,035 A | 5/1975 | Simpson |
| 3,956,495 A | 5/1976 | Lacefield |

(Continued)

FOREIGN PATENT DOCUMENTS

| EP | 194161 A2 | 9/1986 |
| EP | 1803710 A1 | 7/2007 |

(Continued)

OTHER PUBLICATIONS

Hernandes et al., ("Halogen Atoms in the Modern Medicinal Chemistry: Hints for the Drug Design" Current Drug Targets, 2010, 11 pp. 01-12).*

(Continued)

*Primary Examiner* — Susanna Moore
(74) *Attorney, Agent, or Firm* — Viksnins Harris & Padys PLLP

(57) ABSTRACT

The present invention provides a compound and pharmaceutically acceptable salts thereof, comprising the Formula I. Also provided are methods of using the compound of this invention as an AKT protein kinase inhibitor and for the treatment of hyperproliferative diseases such as cancer.

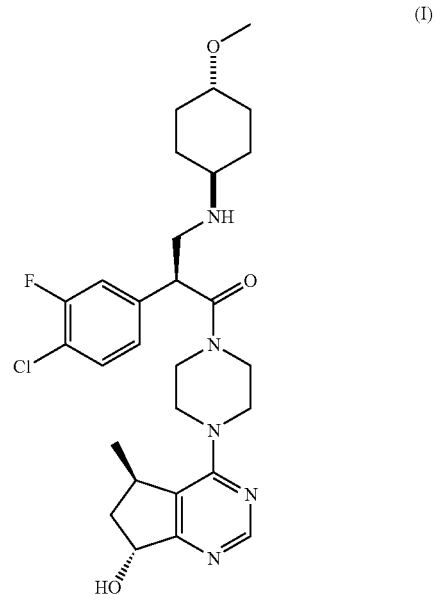

5 Claims, No Drawings

(56) References Cited

U.S. PATENT DOCUMENTS

| | | | |
|---|---|---|---|
| 3,966,936 A | 6/1976 | Cronin et al. | |
| 4,060,615 A | 11/1977 | Matier et al. | |
| 4,352,928 A | 10/1982 | Hiranuma et al. | |
| 5,051,412 A | 9/1991 | Macor | |
| 5,525,625 A | 6/1996 | Bridges et al. | |
| 5,563,152 A | 10/1996 | Kulagowski et al. | |
| 5,610,303 A | 3/1997 | Kimura et al. | |
| 5,750,531 A | 5/1998 | Lee et al. | |
| 5,750,545 A | 5/1998 | Akahoshi et al. | |
| 5,817,671 A | 10/1998 | Filla et al. | |
| 6,310,060 B1 | 10/2001 | Barrett et al. | |
| 6,423,716 B1 | 7/2002 | Matsuno et al. | |
| 6,469,004 B1 | 10/2002 | Barrett et al. | |
| 6,506,798 B1 | 1/2003 | Barrett et al. | |
| 6,627,628 B1 | 9/2003 | Schindler et al. | |
| 6,831,175 B2 | 12/2004 | Li et al. | |
| 7,041,687 B2 | 5/2006 | Binch et al. | |
| 7,067,664 B1 | 6/2006 | Chen | |
| 7,115,741 B2 | 10/2006 | Levy et al. | |
| 7,125,880 B1 | 10/2006 | Chen | |
| 7,223,738 B2 | 5/2007 | Bilodeau et al. | |
| 7,223,767 B2 | 5/2007 | Clark et al. | |
| 8,003,651 B2 | 8/2011 | Mitchell et al. | |
| 8,063,050 B2 * | 11/2011 | Mitchell et al. | 514/252.16 |
| 2003/0004193 A1 | 1/2003 | Barrett et al. | |
| 2003/0045521 A1 | 3/2003 | Tecle | |
| 2003/0078428 A1 | 4/2003 | Barrett et al. | |
| 2003/0092748 A1 | 5/2003 | Barrett et al. | |
| 2003/0199511 A1 | 10/2003 | Li et al. | |
| 2003/0216460 A1 | 11/2003 | Wallace et al. | |
| 2003/0232869 A1 | 12/2003 | Wallace et al. | |
| 2004/0009968 A1 | 1/2004 | Binch et al. | |
| 2004/0053933 A1 | 3/2004 | Pontillo et al. | |
| 2004/0102360 A1 | 5/2004 | Barnett et al. | |
| 2004/0116710 A1 | 6/2004 | Wallace et al. | |
| 2004/0176400 A1 | 9/2004 | Capelli et al. | |
| 2005/0059687 A1 | 3/2005 | Makings et al. | |
| 2005/0130954 A1 | 6/2005 | Mitchell et al. | |
| 2005/0182061 A1 | 8/2005 | Green et al. | |
| 2007/0004708 A1 | 1/2007 | Andreotti et al. | |
| 2007/0027156 A1 | 2/2007 | Nakai et al. | |
| 2007/0135466 A1 | 6/2007 | Ledeboer et al. | |
| 2008/0051399 A1 | 2/2008 | Mitchell et al. | |
| 2008/0076774 A1 | 3/2008 | Anand et al. | |
| 2008/0188482 A1 | 8/2008 | Rice et al. | |

FOREIGN PATENT DOCUMENTS

| | | |
|---|---|---|
| JP | 2009-542720 | 12/2009 |
| JP | 2009-542722 | 12/2009 |
| WO | WO 95/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |
| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/44166 A1 | 6/2002 |
| WO | WO 02/083139 A1 | 10/2002 |
| WO | WO 03/022214 A2 | 3/2003 |
| WO | WO 03/064397 A1 | 8/2003 |
| WO | WO 03/077855 A2 | 9/2003 |
| WO | WO 03/077914 A1 | 9/2003 |
| WO | WO 03/086279 A2 | 10/2003 |
| WO | WO 03/086394 A1 | 10/2003 |
| WO | WO 03/086403 A1 | 10/2003 |
| WO | WO 03/086404 A1 | 10/2003 |
| WO | WO 03/094918 A1 | 11/2003 |
| WO | WO 2004/041162 A2 | 5/2004 |
| WO | WO 2004/096130 A2 | 11/2004 |
| WO | WO 2005/014558 A1 | 2/2005 |
| WO | WO 2005/117909 A2 | 12/2005 |
| WO | WO 2006/046023 A1 | 5/2006 |
| WO | WO 2006/071819 A1 | 7/2006 |
| WO | WO 2006/090261 A1 | 8/2006 |
| WO | WO 2006/136830 A1 | 12/2006 |
| WO | WO 2007/042298 A1 | 4/2007 |
| WO | WO 2007/077961 A2 | 7/2007 |
| WO | WO 2007/125320 A1 | 11/2007 |
| WO | WO 2008/003697 A1 | 1/2008 |
| WO | WO 2008/003958 A2 | 1/2008 |
| WO | WO 2008/003978 A2 | 1/2008 |
| WO | WO 2008/005511 A2 | 1/2008 |
| WO | WO 2008/005964 A2 | 1/2008 |
| WO | WO 2008/006032 A1 | 1/2008 |
| WO | WO 2008/006040 A1 | 1/2008 |
| WO | WO 2008/006583 A1 | 1/2008 |
| WO | WO 2008/012635 A2 | 1/2008 |
| WO | WO 2009/006567 A2 | 1/2009 |
| WO | WO 2009/006569 | 1/2009 |

OTHER PUBLICATIONS

Purser et al. (Chem. Soc. Rev., 2008, 37, pp. 320-330).*

Vippagunta, S.R., *Advanced Drug Delivery Reviews*, vol. 48, pp. 3-26, 2001.

Li, Q., "Recent progress in the discovery of Akt inhibitors as anti-cancer agents", *Expert Opinion: Informa Healthcare 17*(9), pp. 1077-1130, 2007.

Ross, L.O. et al., "Potential Anticancer Agents. XVIII. Synthesis of Substituted 4,5-Trimethylenepyrimidines", *J.Am. Chem. Soc.*, vol. 81, pp. 3108-3113, 1959.

Zhao, Z. et al., "Discovery of 2,3,5-trisubstituted pyridine derivatives as potent Akt1 and Akt2 dual inhibitors," *Bioorganic & Medinical Chemistry Letters*, vol. 15, pp. 905-909, 2005.

Ohno, S. et al., "Synthesis and Hypoglycemic Activity of 7,8-Dihydro-6*H*-thiopyrano[3,2-*d*]pyrimidine Derivatives and Related Compounds", *Chem. Pharm. Bull. 34*(10), pp. 4150-4165, 1986.

Patent Cooperation Treaty, International Search Report and Written Opinion of the International Searching Authority, PCT/US2009/030602, 13 pages, Mar. 31, 2009.

Register of Drugs of Russia, RD, Encyclopedia of Medicines, RLS Publishing House, 1032-1033, 2007 and translation thereof (9 pages).

Office Action and translation thereof issued by the Patent Office of the Russian Federation in Application No. 2010132912, dated Oct. 15, 2012, 8 pages.

Ozhigov, S.I., Explanatory dictionary of the Russian language, Azbukovnuk, Moscow, p. 375, 2004.

Office Action and translation thereof issued by the Patent Office of the Russian Federation in Application No. 2010132911, dated Oct. 15, 2012, 8 pages.

Japanese Office Action for corresponding Japanese Patent Application No. 2010-542373, with English translation, 10 pages, Sep. 17, 2013.

* cited by examiner

HYDROXYLATED PYRIMIDYL CYCLOPENTANE AS AKT PROTEIN KINASE INHIBITOR

JOINT RESEARCH AGREEMENT

The subject matter of this application arises from a joint research agreement pursuant to 35 U.S.C. §103(c)(3) between Array BioPharma, Inc. and Genentech, Inc.

BACKGROUND OF THE INVENTION

1. Field of the Invention

This invention relates to a novel inhibitor of serine/threonine protein kinases (e.g., AKT and related kinases), pharmaceutical compositions containing the inhibitor, and methods for preparing this inhibitor. The inhibitor is useful, for example, for the treatment of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book. I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Significantly, atypical protein phosphorylation and/or expression is often reported to be one of the causative effects of abnormal cellular proliferation, metastasis and cell survival in cancer. The abnormal regulation and/or expression of various kinases, including Akt, VEGF, ILK, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protooncogene v-akt of the acutely transforming retrovirus AKT8. Due to its high sequence homology to protein kinases A and C, Akt is also called Protein Kinase B (PKB) and Related to A and C(RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257:906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)P$_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al. (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The PI3K/Akt/mammalian target of rapamycin (mTOR) pathway has been explored for targeted small molecule inhibitor therapy (Georgakis, G. and Younes, A. (2006) Expert Rev. Anticancer Ther. 6(1):131-140; Granville et al (2006) Clin. Cancer Res. 12(3):679-689) Inhibition of PI3K/Akt signaling induces apoptosis and inhibits the growth of tumor cells that have elevated Akt levels (Kim et al (2005) Current Opinion in Investig. Drugs 6(12):1250-1258; Luo et al (2005) Molecular Cancer Ther. 4(6):977-986).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

United States Patent Application Publication 2005/0130954 discloses inter alia, a variety of compounds that act as AKT inhibitors. The compounds are said to be useful in the treatment of hyperproliferative diseases such as cancer.

SUMMARY OF THE INVENTION

This invention provides a novel compound that inhibits AKT protein kinases. The compound of the present invention has utility as a therapeutic agent for diseases and conditions that can be treated by the inhibition of AKT protein kinases.

More specifically, the present invention includes the compound having the Formula I:

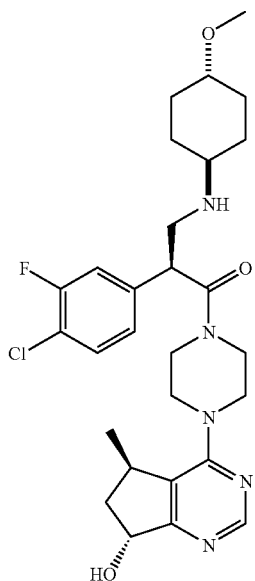

I and pharmaceutically acceptable salts thereof.

The invention also provides pharmaceutical compositions comprising a compound of Formula I or a pharmaceutically acceptable salt thereof.

In a further aspect, the present invention provides a method of treating diseases or medical conditions in a mammal mediated by AKT protein kinases, comprising administering to said mammal a compound of Formula I or a pharmaceutically acceptable salt thereof, in an amount effective to treat or prevent said disorder. AKT protein kinase mediated conditions that can be treated according to the methods of this invention include, but are not limited to, inflammatory, hyperproliferative, cardiovascular, neurodegenerative, gynecological, and dermatological diseases and disorders.

In a further aspect, the present invention provides a method of inhibiting the production of AKT protein kinases in a mammal, which comprises administering to said mammal a compound of Formula I or a pharmaceutically acceptable salt thereof in an amount effective to inhibit production of an AKT protein kinase.

In a further aspect, the present invention provides methods of inhibiting the activity of AKT protein kinases, comprising contacting said kinase with a compound of Formula I.

The inventive compound may be used advantageously in combination with other known therapeutic agents. Accordingly, this invention also provides pharmaceutical compositions comprising a compound of Formula I or a pharmaceutically acceptable salt thereof, in combination with a second therapeutic agent.

This invention also provides the compound of Formula I and pharmaceutically acceptable salts thereof for use as a medicament in the treatment of AKT protein kinase-mediated conditions.

An additional aspect of the invention is the use of a compound of Formula I or a pharmaceutically acceptable salt thereof for therapy. In one embodiment, the therapy comprises the treatment of an AKT protein kinase-mediated condition.

This invention further provides kits for the treatment of an AKT protein kinase-mediated disease or disorder, said kit comprising a compound of Formula I or a pharmaceutically acceptable salt thereof, a container, and optionally a package insert or label indicating a treatment. The kits may further comprise a second compound or formulation comprising a second pharmaceutical agent useful for treating said disease or disorder.

An additional aspect of the present invention provides the use of a compound of Formula I in the treatment of hyperproliferative disease. In a further aspect of this invention the hyperproliferative disease is cancer.

This invention further includes methods of preparing, methods of separating, and methods of purifying the compound of this invention.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "a" as used herein means one or more.

As used herein, the terms "compound of this invention," "compound of the present invention" and "compound of Formula I" includes the compound of Formula I and pharmaceutically acceptable salts thereof.

The phrase "effective amount" means an amount of compound that, when administered to a mammal in need of such treatment, is sufficient to (i) treat or prevent a particular disease, condition, or disorder mediated by the activity of one or more AKT protein kinases, tyrosine kinases, additional serine/threonine kinases, and/or dual specificity kinases, (ii) attenuate, ameliorate, or eliminate one or more symptoms of the particular disease, condition, or disorder, or (iii) prevent or delay the onset of one or more symptoms of the particular disease, condition, or disorder described herein. In the case of cancer, an effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Treating" is intended to mean at least the mitigation of a disease condition in a mammal, such as a human, that is affected, at least in part, by the activity of one or more AKT protein kinases, tyrosine kinases, additional serine/threonine kinases, and/or dual specificity kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those found to be predisposed to having the disease condition but have not yet been diagnosed as having it; modulating and/or inhibiting the disease condition. The terms "treating", "treat", or "treatment" embrace both preventative, i.e., prophylactic, and palliative treatment.

As used herein, the term "mammal" refers to a warm-blooded animal that has or is at risk of developing a disease described herein and includes, but is not limited to, guinea pigs, dogs, cats, rats, mice, hamsters, and primates, including humans.

A "chemotherapeutic agent" is a chemical compound useful in the treatment of cancer, regardless of mechanism of action. Chemotherapeutic agents include compounds used in "targeted therapy" and conventional chemotherapy.

Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)- imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

AKT Inhibitors

The inventive compound of Formula I is useful for inhibiting AKT protein kinases. This compound has utility as a therapeutic agent for diseases that can be treated by the inhibition of the AKT protein kinase signaling pathway and tyrosine and serine/threonine kinase receptor pathways.

In particular, compounds of Formula I having a 7-hydroxy on the cyclopenta[d]pyrimidine were found to be at least 50-fold more selective for AKT versus protein kinase A (PKA). For example, at least 100-fold, and as a further example, at least 150-fold more selective for AKT versus PKA. Selectivity over PKA is desirable, since PKA is involved in many cellular processes important for the normal function and physiology of many cell types. Additionally, inhibition of PKA is not believed to contribute to the anti-proliferative and pro-apoptotic effects of AKT inhibition. Thus, inhibition of PKA could lead to adverse events not associated with AKT inhibition without contributing to the disease modifying benefits of AKT inhibition.

The compound of Formula I may also be useful as an inhibitor of tyrosine kinases as well as serine and threonine kinases in addition to AKT.

In general, one aspect of the invention includes the compound of Formula I:

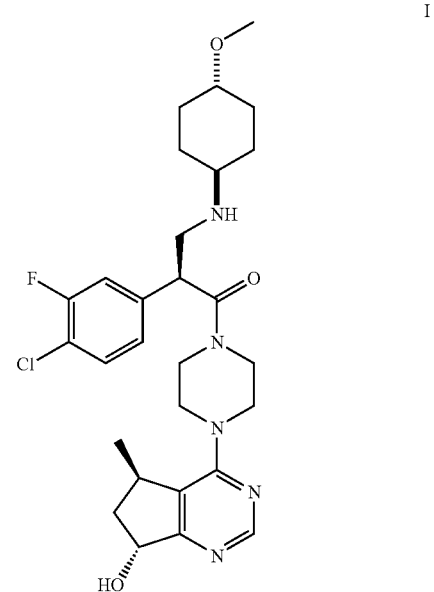 [SMILES: CO[C@H]1CC[C@H](NC[C@@H](C(=O)N2CCN(c3ncnc4c3[C@H](C)C[C@H]4O)CC2)c2ccc(Cl)c(F)c2)CC1]

I and pharmaceutically acceptable salts.

The compound of Formula I includes pharmaceutically acceptable salts of the compound.

The phrase "pharmaceutically acceptable" indicates that the substance or composition is compatible chemically and/or toxicologically with the other ingredients comprising a formulation, and/or the mammal being treated therewith.

Additionally, the compound of the invention may form a salt. Examples of salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compound of Formula I also includes other salts which are not necessarily pharmaceutically acceptable salts, and which may be useful as intermediates for preparing and/or purifying the compound of Formula I and/or for separating the compound of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Synthesis of Compounds of Formula I

The compound of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

For a more detailed description of the individual reaction steps, see the Examples section below. Those skilled in the art will appreciate that other synthetic routes may be used to synthesize the inventive compound. Although specific starting materials and reagents are depicted in the Examples and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing the compound of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing the compound of Formula I, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents ("LIX"), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr.*, (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. $J.$ $Org.$ $Chem.$, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, $J.$ $of$ $Chromatogr.$, (1990) 513: 375-378). Enriched or purified enantiomers can be distinguished by methods used to distinguish other chiral molecules with asymmetric carbon atoms, such as optical rotation and circular dichroism.

Methods of Treatment with Compound of Formula I

The compound of the present invention can be used as prophylactics or therapeutic agents for treating diseases or disorders mediated by modulation or regulation of AKT protein kinases, tyrosine kinases, additional serine/threonine kinases, and/or dual specificity kinases. AKT protein kinase mediated conditions that can be treated according to the methods of this invention include, but are not limited to, inflammatory, hyperproliferative cardiovascular, neurodegenerative, gynecological, and dermatological diseases and disorders.

In one embodiment, said pharmaceutical composition is for the treatment of hyperproliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

The compound and methods of this invention can be also used to treat diseases and conditions such as rheumatoid arthritis, osteoarthritis, Chron's disease, angiofibroma, ocular diseases (e.g., retinal vascularisation, diabetic retinopathy, age-related macular degeneration, macular degeneration, etc.), multiple sclerosis, obesity, Alzheimer's disease, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), septic shock, etc.

Accordingly, another aspect of this invention provides a method of treating diseases or medical conditions in a mammal mediated by AKT protein kinases, comprising administering to said mammal a compound of Formula I or a pharmaceutically acceptable salt thereof in an amount effective to treat or prevent said disorder.

The amount of compound of Formula I that will correspond to such an amount will vary depending upon factors such as the particular compound, disease condition and its severity, the identity (e.g., weight) of the mammal in need of treatment, but can nevertheless be routinely determined by one skilled in the art.

This invention also provides the compound of Formula I for use in the treatment of AKT protein kinase-mediated conditions.

An additional aspect of the invention is the use of the compound of Formula I in the preparation of a medicament for therapy, such as for the treatment or prevention of AKT protein kinase-mediated conditions.

Combination Therapy

The compound of the present invention can be used in combination with one or more additional drugs such as described below. The dose of the second drug can be appropriately selected based on a clinically employed dose. The proportion of the compound of the present invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of the present invention.

The second compound of the pharmaceutical combination formulation or dosing regimen preferably has complementary activities to the compound of this invention such that they do not adversely affect each other. Such drugs are suitably present in combination in amounts that are effective for the purpose intended. Accordingly, another aspect of the present invention provides a composition comprising a compound of this invention in combination with a second drug, such as described herein.

The compound of this invention and the additional pharmaceutically active drug(s) may be administered together in a unitary pharmaceutical composition or separately and, when administered separately this may occur simultaneously or sequentially in any order. Such sequential administration may be close in time or remote in time. The amounts of the compound of this invention and the second drug(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

Routes of Administration

The compound of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use the compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises the compound of this invention. In certain embodiments, the pharmaceutical composition comprises the compound of Formula I in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of the present invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of the present invention may be prepared for various routes and types of administration. For example, a compound of this invention having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the compound of Formula I and, optionally, an additional therapeutic agent) to a mammal. The components of the liposome are commonly arranged in a bilayer formation, similar to the lipid arrangement of biological membranes.

Sustained-release preparations of compounds of this invention may be prepared. Suitable examples of sustained-release preparations include semipermeable matrices of solid hydrophobic polymers containing the compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The pharmaceutical compositions of the compound of this invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of the compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising the compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising the compound of this invention can be used to treat a disorder mediated, for example, by AKT kinase. The label or package insert may also indicate that the composition can be used to treat other disorders.

In certain embodiments, the kits are suitable for the delivery of solid oral forms of the compound of this invention, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with the compound of this invention contained therein; and (b) a second container with a second pharmaceutical formulation contained therein, wherein the second pharmaceutical formulation comprises a second compound useful for treating a disorder mediated by AKT kinase. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of this invention and, if present, the second pharmaceutical formulation. For example, if the kit comprises a first composition comprising the compound of this invention and a second pharmaceutical formulation, the kit may further comprise directions for the simultaneous, sequential or separate administration of the first and second pharmaceutical compositions to a patient in need thereof.

In certain other embodiments wherein the kit comprises a composition of this invention and a second therapeutic agent, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly, a further aspect of this invention provides a kit for treating a disorder or disease mediated by Akt kinase, wherein said kit comprises a) a first pharmaceutical composition comprising the compound of this invention or a pharmaceutically acceptable salt thereof; and b) instructions for use.

In certain embodiments, the kit further comprises (c) a second pharmaceutical composition, wherein the second pharmaceutical composition comprises a second compound suitable for treating a disorder or disease mediated by Akt kinase. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

Although the compound of Formula I is primarily of value as a therapeutic agent for use in mammals, it is also useful whenever it is required to control AKT protein kinases, tyrosine kinases, additional serine/threonine kinases, and/or dual specificity kinases. Thus, it is useful as pharmacological standards for use in the development of new biological tests and in the search for new pharmacological agents.

The activity of the compound of this invention may be assayed for AKT protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLE

AKT-1 Kinase Assay

The activity of the compound described in the present invention may be determined by the following kinase assay, which measures the phosphorylation of a fluorescently-labeled peptide by full-length human recombinant active AKT-1 by fluorescent polarization using a commercially available IMAP kit.

The assay materials are obtained from an IMAP AKT Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM $MgCl_2$, 0.1% BSA, 0.05% $NaN_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled AKT Substrate (Crosstide) has the sequence (Fl)-GRPRTSSFAEG. A stock solution of 20 μM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The AKT-1 used is made from full-length, human recombinant AKT-1 that is activated with PDK1 and MAP kinase 2.

To perform the assay, stock solutions of compounds at 10 mM in dimethylsulfoxide ("DMSO") are prepared. The stock solutions and the control compound are serially diluted 1:2 nine times into DMSO (10 μL of compound+10 μL of DMSO) to give 50× dilution series over the desired dosing range. Next, 2.1-μL aliquots of the compounds in DMSO are transferred to a Costar 3657 plate containing 50 μL of 10.4 μM ATP in 1×IMAP Reaction Buffer containing 1 mM DTT. After thorough mixing, 2.5-μL aliquots are transferred to a ProxyPlate™-384 F plate.

The assay is initiated by the addition of 2.5-μL aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 μL of Binding Solution, centrifuged again and incubated for an additional 30 minutes at ambient temperature prior to reading on a Victor 1420 Multilabel HTS Counter configured to measure fluorescence polarization.

The compound of Example 1 was tested in the above assay and found to have an $IC_{50}$ of less than 500 nM.

PREPARATIVE EXAMPLE

In order to illustrate the invention, the following example is included. However, it is to be understood that this example does not limit the invention and are only meant to suggest a method of practicing the invention. Persons skilled in the art will recognize that the chemical reactions described may be readily adapted to alternative methods for preparing the compound of this invention and are deemed to be within the scope of this invention. For example, the synthesis of the compound of this invention may be successfully prepared by modifications apparent to those skilled in the art, e.g., by appropriately protecting interfering groups, by utilizing other suitable reagents known in the art other than those described, and/or by making routine modifications of reaction conditions. Alternatively, other reactions known in the art will be recognized as having applicability for preparing the compound of the invention.

In the example described below, unless otherwise indicated, all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran ("THF"), dichloromethane ("DCM"), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H NMR spectra were recorded on a Varian instrument operating at 400 MHz. $^1$H-NMR spectra were obtained as $CDCl_3$, $CD_3OD$, $D_2O$ or $d_6$-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

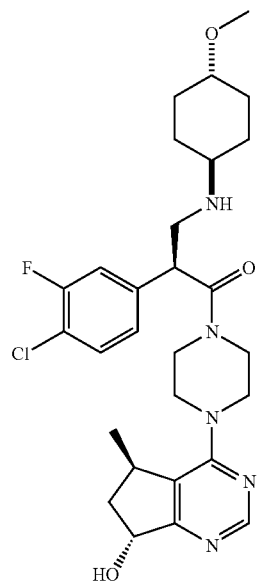

(S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-((1r,4S)-4-methoxycyclohexylamino)propan-1-one

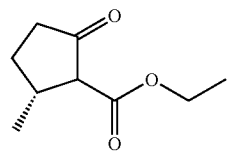

Step 1

Ethyl pulegenate (130 g, 662 mmol) in ethyl acetate ("EtOAc"; 900 mL) was cooled to −78° C. using a dry ice-isopropanol bath. This mixture was subjected to ozonolysis until the reaction turned purple in color. At this point, ozone generation ceased, and the reaction was removed from the dry-ice bath. Oxygen was bubbled through the reaction mixture until it turned yellow. The reaction mixture was concentrated under vacuum, and the resulting residue was dissolved in glacial acetic acid (400 mL). The solution was cooled to 0° C., and Zn dust (65 g, 993 mmol) was added portionwise over 30 minutes. The reaction was then allowed to stir for 2 hours, at which point the reaction mixture was filtered through a pad of celite to remove the zinc dust. The acetic acid was neutralized to a pH of 7 with aqueous NaOH and $NaHCO_3$ and extracted with ether (3×800 mL). The combined organics were dried with brine, MgSO$_4$ and concentrated to give (2R)-ethyl 2-methyl-5-oxocyclopentanecarboxylate as a liquid (107 g, 95%).

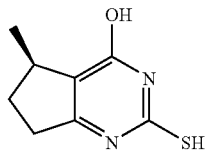

Step 2

KOH (8.3 g, 147.9 mmol) in water (60 mL) was added to a solution of a mixture of (2R)-ethyl 2-methyl-5-oxocyclopentanecarboxylate (20 g, 117.5 mmol) and thiourea (9.2 g, 120.9 mmol) in ethanol (100 mL). The mixture was refluxed for 10 hours. After cooling, the solvent was removed. The resulting residue was neutralized with concentrated HCl (12 mL) at 0° C. and then extracted with DCM (3×150 mL). The solvent was removed, and the resulting residue was purified by silica gel chromatography, eluting with hexane/ethyl acetate (2:1) to give (R)-2-mercapto-5-methyl-6,7-dihydro-5H-cyclopenta[d]pyrimidin-4-ol (12 g, 56%). MS (APCI+) [M+H]+ 183.

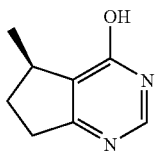

Step 3

Raney Nickel (15 g) and NH$_4$OH (20 mL) was added to a suspension of (R)-2-mercapto-5-methyl-6,7-dihydro-5H-cyclopenta[d]pyrimidin-4-ol (12 g, 65.8 mmol) in distilled water (100 mL). The mixture was refluxed for 3 hours and then filtered. The filtrate was concentrated to afford (R)-5-methyl-6,7-dihydro-5H-cyclopenta[d]pyrimidin-4-ol (9.89 g, 99%). MS (APCI+) [M+H]+151.

Steps 4 and 5 describe an alternate synthesis of (R)-5-methyl-6,7-dihydro-5H-cyclopenta[d]pyrimidin-4-ol, starting from (R)-ethyl 2-methyl-5-oxocyclopentanecarboxylate.

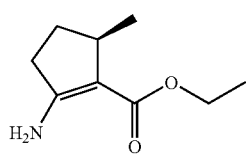

Step 4

Ammonium acetate (240 g, 3114 mmol) was added to a solution of (R)-ethyl 2-methyl-5-oxocyclopentanecarboxylate (106.0 g, 622.8 mmol) in MeOH (1.2 L). The reaction mixture was stirred at room temperature under nitrogen for 20 hours, and the reaction was complete as determined by TLC and HPLC. The reaction mixture was concentrated to remove MeOH. The resulting residue was dissolved in DCM, washed with H$_2$O (2×), brine (1 X), dried (Na$_2$SO$_4$), filtered, and concentrated to give (R)-ethyl 2-amino-5-methylcyclopent-1-enecarboxylate (102 g, 97% yield) as an oil. LC/MS (APCI+) m/z 170 [M+H]+.

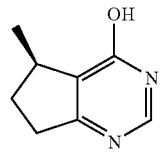

Step 5

A solution containing (R)-ethyl 2-amino-5-methylcyclopent-1-enecarboxylate (161.6 g, 955 mmol) and ammonium formate (90.3 g, 1433 mmol) in formamide (303.5 mL, 7640 mmol) was heated to an internal temperature of 150° C. and stirred for 17 hours. The reaction mixture was cooled, and transferred to a 2 L single nextracted flask. Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried (Na$_2$SO$_4$), filtered, and concentrated. The resulting oil was dissolved in minimal DCM, and this solution was added using a separatory funnel to a stirred solution of ether (about 5 volumes of ether vs. DCM solution), causing some precipitate to form. This precipitate was removed by filtration through a medium fit funnel that was rinsed with ether and disposed. The filtrate was concentrated, and the trituration from ether repeated two more times. The product was then dried on a high vacuum line to give (R)-5-methyl-6,7-dihydro-5H-cyclopenta[d]pyrimidin-4-ol (93.23 g, 65.0% yield) as a pasty solid. LC/MS (APCI−) m/z 149.2.

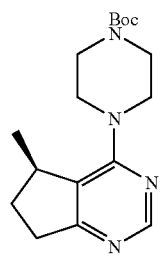 [SMILES: C[C@@H]1CCc2ncnc(N3CCN(C(=O)OC(C)(C)C)CC3)c21]

Step 6

Neat POCl$_3$ (463.9 mL, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to room temperature and then heated to reflux under stirring for 70 minutes. The reaction was complete as determined by HPLC. The reaction mixture was cooled to room temperature, and the excess POCl$_3$ was quenched in 4 portions as follows: Reaction mixture transferred to separatory funnel and dripped into a beaker containing ice and saturated NaHCO$_3$ solution cooled in an ice bath. Once the addition of each portion of the reaction mixture was completed, the quenched mixture was stirred 30 minutes to ensure complete destruction of POCl$_3$ prior to transfer to separatory funnel. The mixture was transferred to the separatory funnel and extracted with DCM (2×). The combined extracts were dried (Na$_2$SO$_4$), filtered, and concentrated. The crude was purified on silica gel as follows: silica gel (1 kg) was slurried in 9:1 hexane:ethyl acetate onto a 3 L fritted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as an oil. Triethylamine (93.0 mL, 534 mmol) and tert-butyl piperazine-1-carboxylate (34.8 g, 187 mmol) were added to a solution of (R)-4-chloro-5-methyl-6,7-dihydro-5H-cyclopenta[d]pyrimidine (30.0 g, 178 mmol) in n-BuOH (250 mL). The reaction mixture was heated to reflux under nitrogen and stirred overnight (17 hours), after which it was concentrated on a rotavap. The resulting oil was dissolved in DCM, washed with H$_2$O, dried (Na$_2$SO$_4$), filtered, and was concentrated. The resulting oil was purified on silica gel eluting first with 2:1 hexanes:ethyl acetate until product eluting cleanly, then gradient 1:1 to 1:5 DCM:ethyl acetate to give (R)-tertbutyl 4-(5-methyl-6,7-dihydro-5H-cyclopenta[d]pyrimidin-4-yl)piperazine-1-carboxylate (42.0 g, 74.1% yield) as a powder. LC/MS (APCI+) m/z 319.1 [M+H]+.

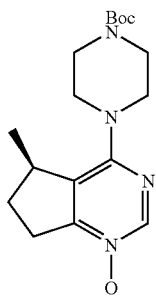

Step 7

Solid 77% max. m-chloroperbenzoic acid ("m-CPBA"; 23.9 g, 107 mmol) was added portionwise to a 0° C. solution of (R)-tert-butyl 4-(5-methyl-6,7-dihydro-5H-cyclopenta[d]pyrimidin-4-yl)piperazine-1-carboxylate (20.0 g, 62.8 mmol) in CHCl$_3$ (310 mL) The reaction mixture was stirred 5 for minutes, then warmed to room temperature and stirred for an additional 90 minutes. HPLC looked similar after 7.5 hours. The reaction mixture was cooled to 0° C., and then NaHCO$_3$ (13.2 g, 157 mmol) and another 0.5 equivalents of m-CPBA were added. The reaction mixture was stirred overnight (14 hours). The reaction mixture was cooled to 0° C., and a solution of Na$_2$S$_2$O$_3$ (29.8 g, 188 mmol) in H$_2$O (50 mL) was added dropwise by addition funnel. This was followed by a solution of Na$_2$CO$_3$ (24.6 g, 232 mmol) in H$_2$O (70 mL) by addition funnel (mixture turns homogeneous). The reaction mixture was stirred for 30 minutes, and then the mixture was extracted with CHCl$_3$ (3×150 mL). The combined extracts were dried (Na$_2$SO$_4$), filtered, and concentrated to give (R)-4-(4-(tert-butoxycarbonyl)piperazin-1-yl)-5-methyl-6,7-dihydro-5H-cyclopenta[d]pyrimidine 1-oxide (21.0 g, 100%). LC/MS (APCI+) m/z 335.1 [M+H]+.

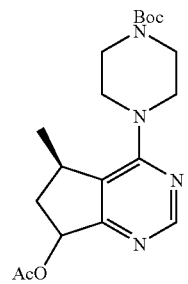 [SMILES: CC(=O)OC1C[C@@H](C)c2c1ncnc2N1CCN(C(=O)OC(C)(C)C)CC1]

Step 8

Ac$_2$O (77.0 mL, 816 mmol) was added to (R)-4-(4-(tert-butoxycarbonyl)piperazin-1-yl)-5-methyl-6,7-dihydro-5H-cyclopenta[d]pyrimidine 1-oxide (21.0 g, 62.8 mmol). The reaction mixture was heated under nitrogen in a 90° C. sand bath and stirred for 100 minutes. The reaction mixture was cooled to room temperature, and excess acetic anhydride was removed by rotary evaporation. The resulting oil was dissolved in DCM, which was then poured carefully into ice saturated Na$_2$CO$_3$. The mixture was extracted with DCM, and the combined extracts were dried (Na$_2$SO$_4$), filtered and concentrated to give (5R)-tert-butyl 4-(7-acetoxy-5-methyl-6,7-dihydro-5H-cyclopenta[d]pyrimidin-4-yl)piperazine-1-carboxylate (23.6 g, 100%) as a foam. LC/MS (APCI+) m/z 377.1 [M+H]+.

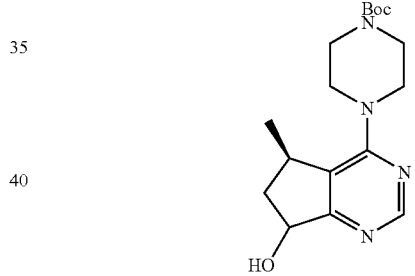

Step 9

LiOH—H$_2$O (6.58 g, 157 mmol) was added to a 0° C. solution of (5R)-tert-butyl 4-(7-acetoxy-5-methyl-6,7-dihydro-5H-cyclopenta[d]pyrimidin-4-yl)piperazine-1-carboxylate (23.6 g, 62.69 mmol) in 2:1 THF:H$_2$O (320 mL). The reaction mixture was stirred for 10 minutes, and then warmed to room temperature. LC/MS looked the same at 3 hours and 4.5 hours. The reaction mixture was cooled to 0° C., and then saturated NH$_4$Cl was added to the mixture. The mixture was stirred for 5 minutes, and most of the THF was removed by rotary evaporation. The mixture was extracted with EtOAc (3×250 mL), and the combined extracts were dried (Na$_2$SO$_4$), filtered, and concentrated. The crude was flashed on Biotage 65M: 4:1 DCM:ethyl acetate, then gradient to 1:1 to 1:4 DCM:ethyl acetate. Once the product was eluting, then ethyl acetate was flushed through the column. Then 30:1 DCM: MeOH eluted the rest of the product (8.83 g). The mixed fractions were re-flashed with Biotage 40M using the same conditions to give another portion (2.99 g), which gave a combined yield of (5R)-tert-butyl 4-(7-hydroxy-5-methyl-6, 7-dihydro-5H-cyclopenta[d]pyrimidin-4-yl)piperazine-1-carboxylate (11.82 g, 56.38% yield) as a foam. LC/MS (APCI+) m/z 335.1 [M+H]+.

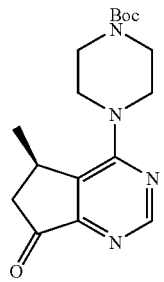 [SMILES: C[C@@H]1CC(=O)c2ncnc(N3CCN(C(=O)OC(C)(C)C)CC3)c21]

Step 10

A solution of DMSO (5.45 mL, 76.8 mmol) in DCM (50 mL) was added dropwise by addition funnel to a −78° C. solution of oxalyl chloride (3.35 mL, 38.4 mmol) in DCM (150 mL). The reaction mixture was stirred for 35 minutes, and then a solution of (5R)-tert-butyl 4-(7-hydroxy-5-methyl-6,7-dihydro-5H-cyclopenta[d]pyrimidin-4-yl)piperazine-1-carboxylate (9.17 g, 27.4 mmol) in DCM (80 mL) was added slowly by addition funnel. The reaction mixture was stirred another 1 hour at −78° C., after which neat triethylamine (18.0 mL, 129 mmol) was added to the mixture. The reaction mixture was then allowed to warm to room temperature, and then it was stirred for 30 minutes. $H_2O$ was added. The mixture was extracted with DCM (3×200 mL), and the combined extracts were dried ($Na_2SO_4$), filtered, and concentrated in vacuo. The crude was purified on silica gel (Biotage 65M): the column was flushed with ca. 800 mL 4:1 DCM:EtOAc, then gradient to 1:1 DCM:ethyl acetate until product eluting, then 1:4 DCM:EtOAc eluted product to give (R)-tert-butyl 4-(5-methyl-7-oxo-6,7-dihydro-5H-cyclopenta[d]pyrimidin-4-yl)piperazine-1-carboxylate (7.5 g, 82.3% yield) as a foam. The foam was concentrated from DCM/hexanes (3×), which also gave a foam. HPLC>95% area. LC/MS (APCI+) m/z 333 [M+H]+.

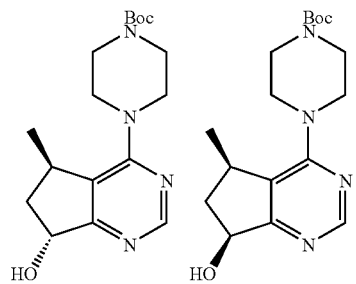

Step 11

Triethylamine (4.33 mL, 31.1 mmol; degassed with nitrogen 30 minutes prior to use) and formic acid (1.36 mL, 36.1 mmol; degassed with nitrogen 30 minutes prior to use) were added to a solution of (R)-tert-butyl 4-(5-methyl-7-oxo-6,7-dihydro-5H-cyclopenta[d]pyrimidin-4-yl)piperazine-1-carboxylate (9.75 g, 29.3 mmol) in DCM (210 mL; degassed with nitrogen 30 minutes prior to use). The mixture was stirred for 5 minutes, and then a Ru catalyst (0.0933 g, 0.147 mmol) was added. The reaction was stirred under positive nitrogen pressure overnight (18 hours). The reaction mixture was concentrated to dryness and dried on high vacuum. The impure material was flashed on Biotage 65M loaded 1:1 DCM:ethyl acetate 500 mL flushed, then 1:4 DCM:ethyl acetate until product (2nd spot), then gradient to neat ethyl acetate, then 25:1 DCM:MeOH eluted rest of product. The fractions were combined and concentrated on a rotary evaporator. The residue was concentrated again from DCM/hexanes to give a mixture of tert-butyl 4-((5R,7R)-7-hydroxy-5-methyl-6,7-dihydro-5H-cyclopenta[d]pyrimidin-4-yl)piperazine-1-carboxylate (major) and tert-butyl 4-((5R,7S)-7-hydroxy-5-methyl-6,7-dihydro-5H-cyclopenta[d]pyrimidin-4-yl)piperazine-1-carboxylate (minor) (9.35 g, 95.3% yield) as a foam. LC/MS (APCI+) m/z 335 [M+H]+. $^1$H NMR ($CDCl_3$) showed 88% diastereoselectivity by integration of carbinol methine.

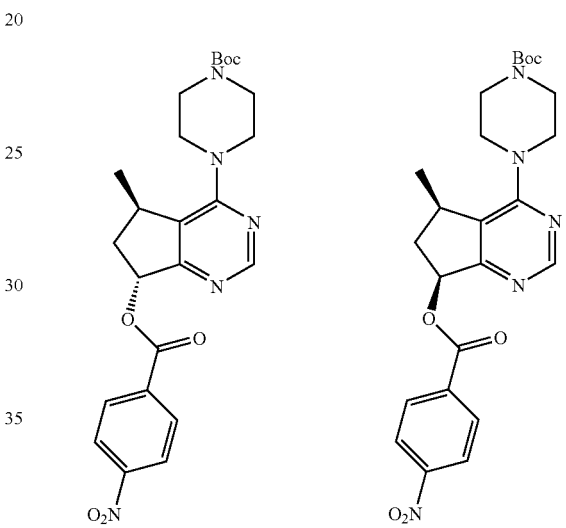

Step 12

4-Nitrobenzoyl chloride (4.27 g, 23.0 mmol) was added to a 0° C. solution of tert-butyl 4-((5R,7R)-7-hydroxy-5-methyl-6,7-dihydro-5H-cyclopenta[d]pyrimidin-4-yl)piperazine-1-carboxylate (7.0 g, 20.9 mmol) and triethylamine (4.38 mL, 31.4 mmol) in DCM (110 mL). The reaction mixture was stirred at room temperature overnight, after which saturated $NaHCO_3$ was added. The mixture was stirred 10 minutes, and then extracted with DCM. The combined extracts were dried ($Na_2SO_4$), filtered, and concentrated. The crude was flashed on Biotage 65M (3:1 hexanes:ethyl acetate loaded crude, then 2:1 hexanes:ethyl acetate eluted tert-butyl 4-((5R,7R)-5-methyl-7-(4-nitrobenzoyloxy)-6,7-dihydro-5H-cyclopenta[d]pyrimidin-4-yl)piperazine-1-carboxylate and a few mixed fractions). Then tert-butyl 4-((5R,7S)-5-methyl-7-(4-nitrobenzoyloxy)-6,7-dihydro-5H-cyclopenta[d]pyrimidin-4-yl)piperazine-1-carboxylate was eluted using 1:2 hexanes:ethyl acetate. The fractions with product were concentrated by rotary evaporation to give tert-butyl 4-((5R,7R)-5-methyl-7-(4-nitrobenzoyloxy)-6,7-dihydro-5H-cyclopenta[d]pyrimidin-4-yl)piperazine-1-carboxylate (8.55 g, 84.5% yield) as a foam. LC/MS (APCI+) m/z 484 [M+H]+. $^1$H NMR ($CDCl_3$) shows single diastereomer). The fractions with the other diastereomer were concentrated by rotary evaporation to give tert-butyl 4-((5R,7S)-5-methyl-7-(4-nitrobenzoyloxy)-6,7-dihydro-5H-cyclopenta[d]pyrimidin-4-yl)piperazine-1-carboxylate (0.356 g, 3.52% yield) as a foam. LC/MS (APCI+) m/z 484 [M+H]+.

Step 13 describes an alternative preparation of tert-butyl 4-((5R,7S)-5-methyl-7-(4-nitrobenzoyloxy)-6,7-dihydro-5H-cyclopenta[d]pyrimidin-4-yl)piperazine-1-carboxylate and tert-butyl 4-((5R,7R)-5-methyl-7-(4-nitrobenzoyloxy)-6,7-dihydro-5H-cyclopenta[d]pyrimidin-4-yl)piperazine-1-carboxylate from (5R)-tert-butyl 4-(7-hydroxy-5-methyl-6,7-dihydro-5H-cyclopenta[d]pyrimidin-4-yl)piperazine-1-carboxylate (Step 9).

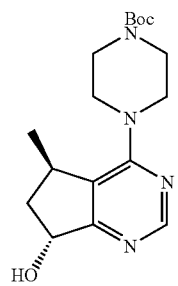

Step 14

LiOH—H$_2$O (0.499 g, 11.9 mmol) was added to a 0° C. solution of tert-butyl 4-((5R,7R)-5-methyl-7-(4-nitrobenzoyloxy)-6,7-dihydro-5H-cyclopenta[d]pyrimidin-4-yl)piperazine-1-carboxylate (2.30 g, 4.76 mmol) in 2:1 THF:H$_2$O (40 mL). The reaction mixture was warmed to room temperature and stirred for 1 hour. The THF was removed by rotary evaporation. Saturated NaHCO$_3$ was then added, and the mixture was extracted with ethyl acetate. The combined extracts were washed (1×) with saturated NaHCO$_3$, dried (Na$_2$SO$_4$), filtered, and concentrated to give tert-butyl 4-((5R,7R)-7-hydroxy-5-methyl-6,7-dihydro-5H-cyclopenta[d]pyrimidin-4-yl)piperazine-1-carboxylate (1.59 g, 100.0% yield) as a foam. HPLC after workup just product gave greater thab 98% area pure. LC/MS (APCI+) m/z 335 [M+H]+.

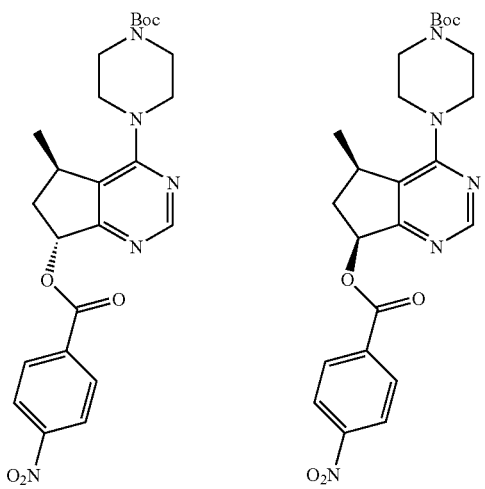 [SMILES: C[C@@H]1C[C@@H](OC(=O)c2ccc([N+](=O)[O-])cc2)c2ncnc(N3CCN(C(=O)OC(C)(C)C)CC3)c21 ; C[C@@H]1C[C@H](OC(=O)c2ccc([N+](=O)[O-])cc2)c2ncnc(N3CCN(C(=O)OC(C)(C)C)CC3)c21]

Step 13

4-Nitrobenzoyl chloride (15.78 g, 85.03 mmol) was added to a 0° C. solution of (R)-tert-butyl 4-(7-hydroxy-5-methyl-6,7-dihydro-5H-cyclopenta[d]pyrimidin-4-yl)piperazine-1-carboxylate (25.85 g, 77.30 mmol) and NEt$_3$ (11.73 g, 16.16 mL, 115.9 mmol) in DCM (400 mL). The reaction mixture was stirred for 5 minutes. The mixture was then warmed to room temperature and stirred overnight (17 hours), after which saturated NaHCO$_3$ was added. The reaction mixture was stirred for 10 minutes and transferred to a separatory funnel. The organic layers were collected, and the aqueous extracts were washed with DCM (2 X). The combined organic extracts were dried (Na$_2$SO$_4$), filtered, and concentrated. The crude was flashed on silica loaded with 7:1 hexanes:ethyl acetate (gradient 5:1 hexanes:ethyl acetate to 2:1 hexanes:ethyl acetate to 1:1 hexanes:ethyl acetate). Some clean tert-butyl 4-((5R,7R)-5-methyl-7-(4-nitrobenzoyloxy)-6,7-dihydro-5H-cyclopenta[d]pyrimidin-4-yl)piperazine-1-carboxylate, some clean tert-butyl 4-((5R,7S)-5-methyl-7-(4-nitrobenzoyloxy)-6,7-dihydro-5H-cyclopenta[d]pyrimidin-4-yl)piperazine-1-carboxylate and some mixed fractions were isolated. The mixed fractions were recolumned and combined with the previously isolated material to give tert-butyl 4-((5R,7R)-5-methyl-7-(4-nitrobenzoyloxy)-6,7-dihydro-5H-cyclopenta[d]pyrimidin-4-yl)piperazine-1-carboxylate (14.27 g, 38%) and tert-butyl 4-((5R,7S)-5-methyl-7-(4-nitrobenzoyloxy)-6,7-dihydro-5H-cyclopenta[d]pyrimidin-4-yl)piperazine-1-carboxylate (12.58 g, 34%). The use of 4-bromobenzoyl chloride has been shown to offer slightly better separation of the isomers.

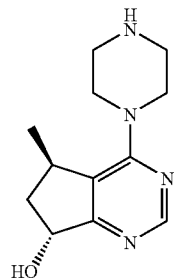

Step 15

4M HCl/dioxane (11.2 mL, 44.9 mmol) was added to a solution of tert-butyl 4-((5R,7R)-7-hydroxy-5-methyl-6,7-dihydro-5H-cyclopenta[d]pyrimidin-4-yl)piperazine-1-carboxylate (0.600 g, 1.79 mmol) in dioxane (15 mL). The reaction mixture was stirred at room temperature under nitrogen overnight (20 hours). The mixture was concentrated to dryness and dried on a high vacuum line. The crude was suspended in ether, sonicated, and stirred for 5 minutes. The solids were isolated by filtration through a medium frit funnel with nitrogen pressure, rinsed with ether, dried under nitrogen pressure, and dried further on a high vacuum line to give (5R,7R)-5-methyl-4-(piperazin-1-yl)-6,7-dihydro-5H-cyclopenta[d]pyrimidin-7-ol dihydrochloride (0.440 g, 79.8% yield) as a powder. LC/MS (APCI+) m/z 235.

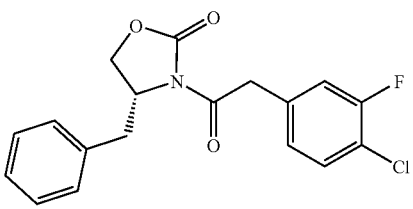 [SMILES: O=C(Cc1ccc(Cl)c(F)c1)N1C(=O)OC[C@H]1Cc1ccccc1]

Step 16

Trimethylacetyl chloride (1.68 g, 13.9 mmol) was added to a solution of 2-(4-chloro-3-fluorophenyl)acetic acid (2.50 g, 13.3 mmol) and TEA (d. 0.726; 2.00 mL, 14.3 mmol) in dry THF (100 mL) at 0° C. and stirred at room temperature. In a separate flask, n-BuLi (6.424 mL, 14.58 mmol) was added to (R)-4-benzyloxazolidin-2-one (2.47 g, 13.9 mmol) in dry THF (100 mL) at −78° C. The reaction was strirred for 20 minutes at −78° C., and then the (R)-4-benzyloxazolidin-2-one solution was added dropwise to the 0° C. mixed anhydride solution. The reaction was allowed to stir overnight at room temperature. The reaction was quenched with water (100 mL) and diluted with ethyl acetate (100 mL). The layers were separated, and the organics were washed with brine, dried (MgSO$_4$) and concentrated to a residue. The resulting residue was purified by flash chromatography to give (R)-4-benzyl-3-(2-(4-chloro-3-fluorophenyl)acetyl)oxazolidin-2-one (2.79 g, 8.02 mmol, 60.5% yield). $^1$H NMR (400 MHz, CDCl$_3$) 7.37 (t, J=8.2 Hz, 1H), 7.33-7.26 (m, 3H), 7.18-7.12 (m, 3H), 7.07 (d, J=8.2 Hz, 1H), 4.73-4.65 (m, 1H), 4.33-4.18 (m, 4H), 3.27 (dd, J1=3.5 Hz, J2=13.3 Hz, 1H), 2.77 (dd, J1=9.4 Hz, J2=13.7 Hz, 1H).

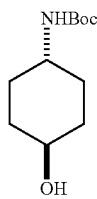 [SMILES: CC(C)(C)OC(=O)N[C@H]1CC[C@H](O)CC1]

Step 17

(1r,4r)-4-Aminocyclohexanol hydrochloride (6.67 g, 44 mmol) was suspended in DCM (100 mL). Huning's base (15 mL) was then added, followed by the addition of catalytic 4-dimethylaminopyridine ("DMAP"). The reaction was stirred for 5 minutes, and then Boc$_2$O (10.2 g, 47 mmol) was added portionwise over 10 minutes. The reaction was then allowed to stir overnight at room temperature. The reaction was quenched by the addition of 1N HCl and allowed to stir for 10 minutes. The organic layer was separated, and the aqueous layer was washed with DCM (2×). The combined organics were then dried with brine and MgSO$_4$ and concentrated. The resulting residue was suspended into hexanes (removal of any excess Boc$_2$O) and filtered. The desired material was obtained as solid tert-butyl (1r,4r)-4-hydroxycyclohexylcarbamate (5.1 g, 54% yield). $^1$H NMR (400 MHz, CDCl$_3$) 4.35 (br s, 1H), 3.65-3.52 (m, 1H), 3.43 (br s, 1H), 1.99 (apparent triplet, J1=17.2 Hz, J2=12.1 Hz, 4H), 1.49-1.30 (m, 12H), 1.4-1.08 (m, 2H).

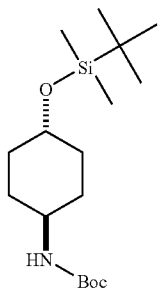 [SMILES: CC(C)(C)OC(=O)N[C@H]1CC[C@H](O[Si](C)(C)C(C)(C)C)CC1]

Step 18

NEt$_3$ (d. 0.726; 4.95 mL, 35.5 mmol) was added at room temperature to a solution of tert-butyl (1r,4r)-4-hydroxycyclohexylcarbamate (5.1 g, 23.7 mmol) in DCM (100 mL) and stirred as a suspension. The reaction stirred for 10 minutes followed by addition of tert-butyldimethylsilyl trifluoromethanesulfonate (6.52 mL, 26.1 mmol), upon which the reaction became a homogenous solution and was stirred for 2 hours. The reaction was diluted with water (50 mL) and the layers were separated. The organics were washed with 1N HCl (2×50 mL), dried (MgSO$_4$) and concentratedentrated to a solid. The solid was purified by flash chromatography (5% ethyl acetate/hexanes) to give tert-butyl (1r,4r)-4-(tert-butyldimethylsilyloxy)cyclohexylcarbamate (6.54 g, 19.8 mmol, 83.8% yield). $^1$H NMR (400 MHz, CDCl$_3$) 4.34 (br s, 1H), 3.61-3.50 (m, 1H), 3.4 (br s, 1H), 1.97 (d, J=12.9 Hz, 2H), 1.82 (d, J=13.7 Hz, 2H), 1.44 (s, 9H), 1.43-1.30 (m, 2H), 1.21-1.05 (m, 2H), 0.87 (s, 9H), 0.04 (s, 6H).

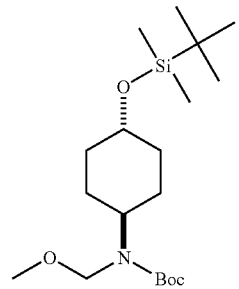 [SMILES: COCN(C(=O)OC(C)(C)C)[C@H]1CC[C@H](O[Si](C)(C)C(C)(C)C)CC1]

Step 19

A solution of tert-butyl (1r,4r)-4-(tert-butyldimethylsilyloxy)cyclohexylcarbamate (1.00 g, 3.03 mmol) in dry THF (50 mL) was cooled to −78° C. n-BuLi (1.27 mL, 3.19 mmol) was then added. The reaction was stirred for 20 minutes with warming to −40° C. This was followed by fast dropwise addition of chloromethyl methyl ether (d=1.060; 0.254 mL, 3.34 mmol). The cold bath was removed, and the reaction was stirred with warming under nitrogen. The reaction was quenched with water, and extractive work-up and purification by flash chromatography (5% ethyl acetate/hexanes) provided tert-butyl (1r,4r)-4-(tert-butyldimethylsilyloxy)cyclohexyl(methoxymethyl)carbamate (0.957 g, 2.36 mmol, 84% yield). $^1$H NMR (400 MHz, CDCl$_3$) 4.69 (br s, 1H), 3.85-3.47 (m, 1H), 3.27 (s, 3H), 1.90 (d, J=10.5 Hz, 2H), 1.79 (d, J=12.9 Hz, 2H), 1.67-1.50 (m, 2H), 1.47 (s, 9H), 1.46-1.30 (m, 4H), 0.88 (s, 9H), 0.04 (s, 6H).

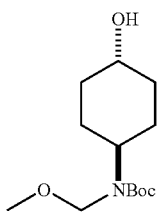 [SMILES: COCN(C(=O)OC(C)(C)C)[C@H]1CC[C@H](O)CC1]

Step 20

Tetrabutylammonium fluoride (8.94 mL, 8.94 mmol) was added to a solution of tert-butyl (1r,4r)-4-(tert-butyldimethylsilyloxy)cyclohexylcarbamate (1.97 g, 5.96 mmol) in THF (50 mL) and heated to 40° C. overnight. The reaction was diluted with water (100 mL) and ethyl acetate (100 mL). The layers were then separated, and the organics were dried (MgSO$_4$) and concentrated to an oil. The oil was purified by flash chromatography (25% ethyl acetate/hexanes) to give tert-butyl (1r,4r)-4-hydroxycyclohexyl(methoxymethyl)carbamate (1.32 g, 5.09 mmol, 85% yield).

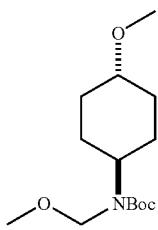

Step 21

NaH (60% in oil; 0.563 g, 14.07 mmol) was added to a solution of tert-butyl (1r,4r)-4-hydroxycyclohexyl(methoxymethyl)carbamate (3.65 g, 14.07 mmol) in THF (50 mL) and heated to 40° C. Methyl iodide (0.878 mL, 14.07 mmol) was added to the warm stirring solution and heated to 60° C. overnight. The reaction was quenched with water (100 mL) and diluted with ethyl acetate (100 mL). The layers were then separated. The organics were dried (MgSO$_4$) and concentrated. The resulting residue was purified by flash chromatography (10% ethyl acetate/hexanes) to give tert-butyl (1r,4r)-4-methoxycyclohexyl(methoxymethyl)carbamate (3.51 g, 12.8 mmol, 91% yield).

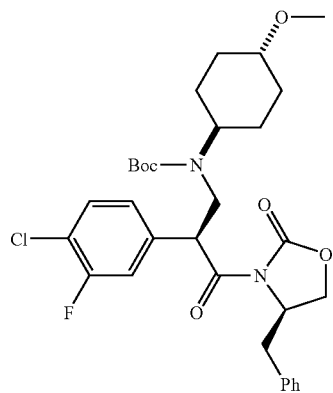

Step 22

TiCl$_4$ (0.207 g, 1.09 mmol) was added to a solution cooled to −78° C. of (R)-4-benzyl-3-(2-(4-chloro-3-fluorophenyl)acetyl)oxazolidin-2-one (0.362 g, 1.04 mmol) and (1r,4r)-4-methoxycyclohexyl(methoxymethyl)carbamate (0.55 g, 2.01 mmol) in dry DCM (20 mL). Diisopropylethylamine ("DIEA"; d 0.742; 0.199 mL, 1.15 mmol) was added to this cold stirring solution. The reaction was stirred for 15 minutes at −78° C. and then warmed to −10° C. and stirred for 3 hours. The reaction was quenched with NH$_4$Cl. The reaction was diluted with DCM (50 mL) and water (50 mL). The layers were then separated. The aqueous layer was extracted with DCM (25 mL), dried (MgSO$_4$) and concentrated to an oil. The oil was purified by column chromatography (10% Et$_2$O/hexanes to 30% Et$_2$O/hexanes) to give tert-butyl (S)-3-((R)-4-benzyl-2-oxooxazolidin-3-yl)-2-(4-chloro-3-fluorophenyl)-3-oxopropyl((1r,4S)-4-methoxycyclohexyl)carbamate (0.610 g, 1.04 mmol, 99.5% yield). $^1$H NMR (400 MHz, CDCl$_3$) 7.38-7.28 (m, 4H), 7.25-7.15 (m, 3H), 7.10 (d, J=8.6 Hz, 1H), 4.65-4.56 (m, 1H), 4.15-4.03 (m, 2H), 3.60-3.36 (m, 2H), 3.31 (s, 3H), 3.15-2.95 (m, 1H), 2.12-1.97 (m, 3H), 1.69-1.57 (m, 2H), 1.47 (s, 9H), 1.46-1.37 (m, 3H), 1.37-1.07 (m, 4H).

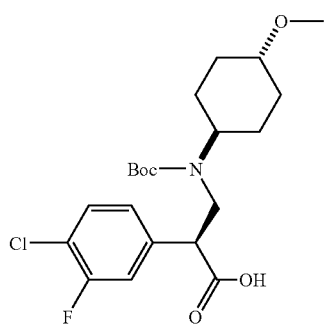

Step 23

H$_2$O$_2$ (0.294 mL, 3.06 mmol) was added to a solution of LiOH—H$_2$O (0.0855 g, 2.04 mmol) in THF/water (2:1, 83 mL). The solution was stirred at room temperature for 10 minutes. The solution was cooled to 0° C. and treated with a solution of tert-butyl (S)-3-((R)-4-benzyl-2-oxooxazolidin-3-yl)-2-(4-chloro-3-fluorophenyl)-3-oxopropyl((1r,4S)-4- methoxycyclohexyl)carbamate (0.600 g, 1.019 mmol) in THF (10 mL). The reaction was stirred at 0° C. for 2 hours and then allowed to warm to room temperature and stirred overnight. The reaction was cooled to 0° C. and treated with 1M $Na_2SO_3$ (10 mL) and stirred for 10 minutes. The reaction was then warmed to room temperature and stirred for 10 minutes. The reaction was concentrated and extracted with ethyl acetate (2×20 mL). The aqueous portion was acidified with $HSO_4$ (s) to a pH of about 1 to about 2 and then extracted with DCM (2×20 mL). The organics were combined, dried ($MgSO_4$) and concentrated. The resulting residue provided (S)-3-(tert-butoxycarbonyl((1r,4S)-4-methoxycyclohexyl)amino)-2-(4-chloro-3-fluorophenyl)propanoic acid (0.312 g, 0.726 mmol, 71% yield). LC/MS>95% purity, r.t.=3.25 minutes, (APCI+) m/z=430 [M+H]+.

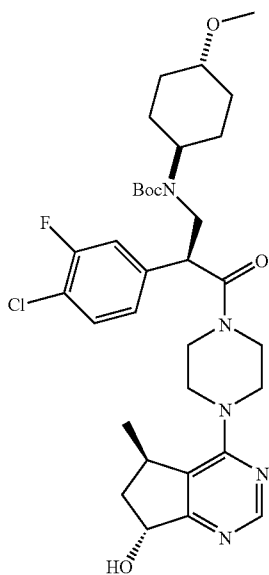 [SMILES: CO[C@H]1CC[C@H](N(C[C@@H](C(=O)N2CCN(c3ncnc4c3[C@H](C)C[C@H]4O)CC2)c2ccc(Cl)c(F)c2)C(=O)OC(C)(C)C)CC1]

Step 24

(5R,7R)-5-Methyl-4-(piperazin-1-yl)-6,7-dihydro-5H-cyclopenta[d]pyrimidin-7-ol dihydrochloride (0.236 g, 0.768 mmol), O-(7-azabenzotriazol-1-yl)-N,N,N',N'-tetramethyluronium hexafluorophosphate ("HATU"; 0.265 g, 0.698 mmol) and collidine (0.369 mL, 2.79 mmol) were added to a solution of (S)-3-(tert-butoxycarbonyl((1r,4S)-4-methoxycyclohexyl)amino)-2-(4-chloro-3-fluorophenyl)propanoic acid (0.300 g, 0.698 mmol) in DCM/DMF (15 mL, 2:1), and the reaction was stirred overnight at room temperature. The reaction was partioned between water (20 mL) and DCM (50 mL), and the layers were separated. The organic layer was washed with water (2×10 mL), The aqueous layer was back extracted with DCM (25 mL), dried ($MgSO_4$) and concentrated to an oil. The oil was purified by column chromatography (5% MeOH/DCM) to give tert-butyl (S)-2-(4-chloro-3-fluorophenyl)-3-(4-((5R,7R)-7-hydroxy-5-methyl-6,7-dihydro-5H-cyclopenta[d]pyrimidin-4-yl)piperazin-1-yl)-3-oxopropyl((1r,4S)-4-methoxycyclohexyl)carbamate (0.394 g, 0.610 mmol, 87.4% yield). LC/MS>95% purity, r.t.=3.83 minutes, (APCI+) m/z=646.

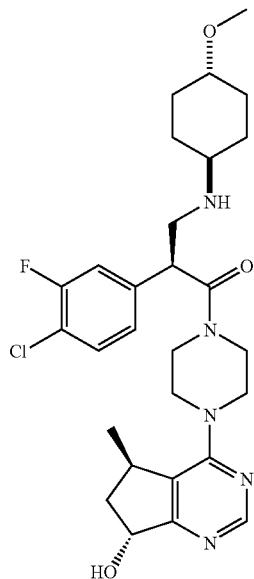

Step 25

4N HCl in dioxane (4 mL, 16 mmol) was added to a solution of tert-butyl (S)-2-(4-chloro-3-fluorophenyl)-3-(4-((5R,7R)-7-hydroxy-5-methyl-6,7-dihydro-5H-cyclopenta[d]pyrimidin-4-yl)piperazin-1-yl)-3-oxopropyl((1r,4S)-4-methoxycyclohexyl)carbamate (0.370 g, 0.573 mmol) in DCM (10 mL), and the reaction was stirred at room temperature for 3 hours. The reaction contents were added dropwise to a vigorously stirred mixture of $Et_2O$/hexanes (75 mL, 3:1) giving a solid as fine particles. The particles were filtered and dried to give (S)-2-(4-chloro-3-fluorophenyl)-1-(4-((5R,7R)-7-hydroxy-5-methyl-6,7-dihydro-5H-cyclopenta[d]pyrimidin-4-yl)piperazin-1-yl)-3-((1r,4S)-4-methoxycyclohexylamino)propan-1-one dihydrochloride (0.325 g, 0.525 mmol, 91.7% yield). LC/MS>95% purity, r.t.=2.52 minutes, (APCI+) m/z=546.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A compound of Formula I:

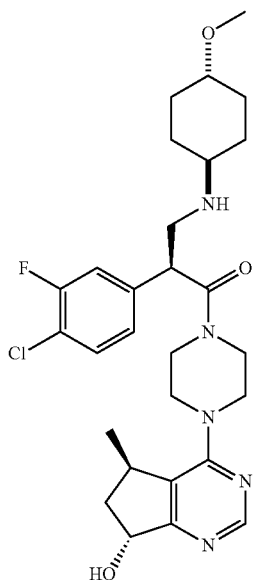

or a pharmaceutically acceptable salt thereof.

2. A pharmaceutical composition comprising a compound as claimed in claim 1 or a pharmaceutically acceptable salt thereof and a pharmaceutically acceptable diluent or carrier.

3. A kit, wherein said kit comprises:

a) a first pharmaceutical composition comprising a compound as claimed in claim 1 or a pharmaceutically acceptable salt thereof; and b) optionally instructions for use.

4. A method of inhibiting AKT activity in a mammal in need thereof, comprising administering to said mammal a therapeutically effective amount of a compound as claimed in claim 1 or a pharmaceutically acceptable salt thereof.

5. The method of claim 4, wherein said mammal is suffering from an inflammatory, hyperproliferative, cardiovascular, neurodegenerative, gynecological, or dermatological disease or disorder.

* * * * *